US012666143B2

(12) United States Patent
Quinn et al.

(10) Patent No.: US 12,666,143 B2
(45) Date of Patent: Jun. 23, 2026

(54) MODULAR MONITORING SYSTEMS AND METHODS

(71) Applicant: Welch Allyn, Inc., Skaneateles Falls, NY (US)

(72) Inventors: David Quinn, Skaneateles Falls, NY (US); Gene J. Wolfe, Skaneateles Falls, NY (US); WonKyung McSweeney, Skaneateles Falls, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 128 days.

(21) Appl. No.: 18/815,281

(22) Filed: Aug. 26, 2024

(65) Prior Publication Data

US 2025/0080837 A1     Mar. 6, 2025

Related U.S. Application Data

(60) Provisional application No. 63/579,401, filed on Aug. 29, 2023.

(51) Int. Cl.
H04N 23/661          (2023.01)
G16H 40/63          (2018.01)
(Continued)

(52) U.S. Cl.
CPC ........... H04N 23/661 (2023.01); G16H 40/63 (2018.01); H04N 23/45 (2023.01); H04N 23/51 (2023.01); H04N 23/57 (2023.01)

(58) Field of Classification Search
CPC ...... H04N 23/661; H04N 23/51; H04N 23/57; H04N 23/45; G16G 40/63
See application file for complete search history.

(56) References Cited

U.S. PATENT DOCUMENTS

| | | | |
|---|---|---|---|
| 5,640,953 A | 6/1997 | Bishop et al. | |
| 10,116,776 B2 * | 10/2018 | Jannard ................. | H04N 23/55 |

(Continued)

FOREIGN PATENT DOCUMENTS

| | | |
|---|---|---|
| WO | 2015094248 A1 | 6/2015 |
| WO | 2019162981 A1 | 8/2019 |

OTHER PUBLICATIONS

International Search Report for Appln. No. PCT/US2024/044038 mailed Dec. 18, 2024, 15 pages.

*Primary Examiner* — Nicholas G Giles
(74) *Attorney, Agent, or Firm* — Dinsmore & Shohl LLP

(57)          ABSTRACT

A modular monitor system includes a processor; a plurality of slots including a predetermined shape; a plurality of image acquisition devices configured to be received in any one of the plurality of slots and communicatively coupled with the processor; and a non-transitory, processor readable storage medium communicatively coupled to the processor that includes one or more instructions stored thereon that, when executed, cause the processor to: obtain acquisition data; prioritize selection, based on the acquisition data, of one or more image acquisition devices from the plurality of image acquisition devices in accordance with predetermined criteria, the predetermined criteria including a computational load, image acquisition device availability, image acquisition device cost, one or more use cases, or any combination thereof, the respective ones of the one or more image acquisition devices including a different modality; and control, based on the prioritized selection, operation of the one or more image acquisition devices.

20 Claims, 6 Drawing Sheets

(51) Int. Cl.

| | |
|---|---|
| *H04N 23/45* | (2023.01) |
| *H04N 23/51* | (2023.01) |
| *H04N 23/57* | (2023.01) |

(56) References Cited

U.S. PATENT DOCUMENTS

| | | | | |
|---|---|---|---|---|
| 10,354,504 | B2 | 7/2019 | Kiani et al. | |
| 10,568,499 | B2 * | 2/2020 | Tesar | A61B 1/00154 |
| 12,199,378 | B2 * | 1/2025 | Lund | H01R 13/64 |
| 2017/0171371 | A1 * | 6/2017 | Jannard | H04N 23/45 |
| 2019/0053700 | A1 * | 2/2019 | Tesar | G02B 21/368 |
| 2021/0057851 | A1 | 2/2021 | Lund et al. | |
| 2021/0158937 | A1 | 5/2021 | Wu et al. | |
| 2021/0256267 | A1 | 8/2021 | Ranasinghe et al. | |
| 2021/0369240 | A1 | 12/2021 | Moss, Jr. | |
| 2022/0061671 | A1 | 3/2022 | Dacosta et al. | |
| 2023/0000358 | A1 | 1/2023 | Addison | |
| 2023/0057855 | A1 | 2/2023 | Soreefan et al. | |
| 2023/0091003 | A1 | 3/2023 | Zapata et al. | |
| 2023/0335951 | A1 * | 10/2023 | Lund | H01R 13/642 |

* cited by examiner

MODULAR MONITORING SYSTEMS AND METHODS

CROSS-REFERENCE TO RELATED APPLICATIONS

This application claims priority to U.S. Provisional Patent Application Ser. No. 63/579,401, filed Aug. 29, 2023, entitled, "MODULAR MONITORING SYSTEMS AND METHODS," the entirety of which is incorporated by reference herein.

FIELD

The present disclosure generally relates to monitoring devices, and more particularly, to systems and methods that prioritize and selectively control devices for monitoring objects in a space.

BACKGROUND

Monitoring of objects in a space, such as a subject in a medical surgical room, is useful for achieving timely and optimal subject care. The absence of personnel (e.g., a nurse or assistant) within the space adds complexity, as the subject is not promptly attended to nor sufficiently monitored for receiving appropriate medication and care. Conventional virtual monitoring analysis systems for use in various subject use cases are designed to account for different environments and various clinical acuities of the subject to be monitored. However, these environments and clinical acuities are highly variable.

In addition, to completely cover the entire universe of use cases requires a system that contains all available modalities, which would be undesirable and untenable from various technical and non-technical standpoints. Relatedly, no single subject, even high acuity subjects, would require every monitoring modality.

SUMMARY

In one aspect, a modular monitor system may include a processor; a plurality of slots that each include a predetermined shape; a plurality of image acquisition devices configured to be received in any one of the plurality of slots and communicatively coupled with the processor; and a non-transitory, processor readable storage medium communicatively coupled to the processor. The non-transitory, processor readable storage medium include one or more instructions stored thereon that, when executed, cause the processor to obtain acquisition data. The non-transitory, processor readable storage medium include one or more instructions stored thereon that, when executed, cause the processor to prioritize selection, based on the acquisition data, of one or more image acquisition devices from the plurality of image acquisition devices in accordance with predetermined criteria. The predetermined criteria may include a computational load, image acquisition device availability, image acquisition device cost, one or more use cases, or any combination thereof. The respective ones of the one or more image acquisition devices may include a different modality. The non-transitory, processor readable storage medium include one or more instructions stored thereon that, when executed, cause the processor to control, based on the prioritized selection, operation of the one or more image acquisition devices selected from the plurality of image acquisition devices.

In another aspect, a method to be performed by a processor of a computing device is provided. The method may include obtaining acquisition data. The method may include prioritizing selection, based on the acquisition data, of one or more image acquisition devices from a plurality of image acquisition devices in accordance with predetermined criteria. The predetermined criteria may include a computational load, image acquisition device availability, image acquisition device cost, one or more use cases, or any combination thereof. The method may include the plurality of image acquisition devices being configured to be received in any one of a plurality of slots that each include a predetermined shape. The respective ones of the one or more image acquisition devices may include a different modality. The method may include controlling, based on the prioritized selection, operation of the one or more image acquisition devices selected from the plurality of image acquisition devices.

In another aspect, a non-transitory, computer-readable medium including instructions that, when executed by at least one processor, cause the at least one processor to perform one or more operations including obtaining acquisition data. The instructions that, when executed by the at least one processor, cause the at least one processor to perform one or more operations including prioritizing selection, based on the acquisition data, of one or more image acquisition devices from a plurality of image acquisition devices in accordance with predetermined criteria. The predetermined criteria may include a computational load, image acquisition device availability, image acquisition device cost, one or more use cases, or any combination thereof. The plurality of image acquisition devices may be configured to be received in any one of a plurality of slots that each include a predetermined shape. The respective ones of the one or more image acquisition devices may include a different modality. The instructions that, when executed by the at least one processor, cause the at least one processor to perform one or more operations including controlling, based on the prioritized selection, operation of the one or more image acquisition devices selected from the plurality of image acquisition devices.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, wherein like structure is indicated with like reference numerals and in which:

DETAILED DESCRIPTION

Figure 1:
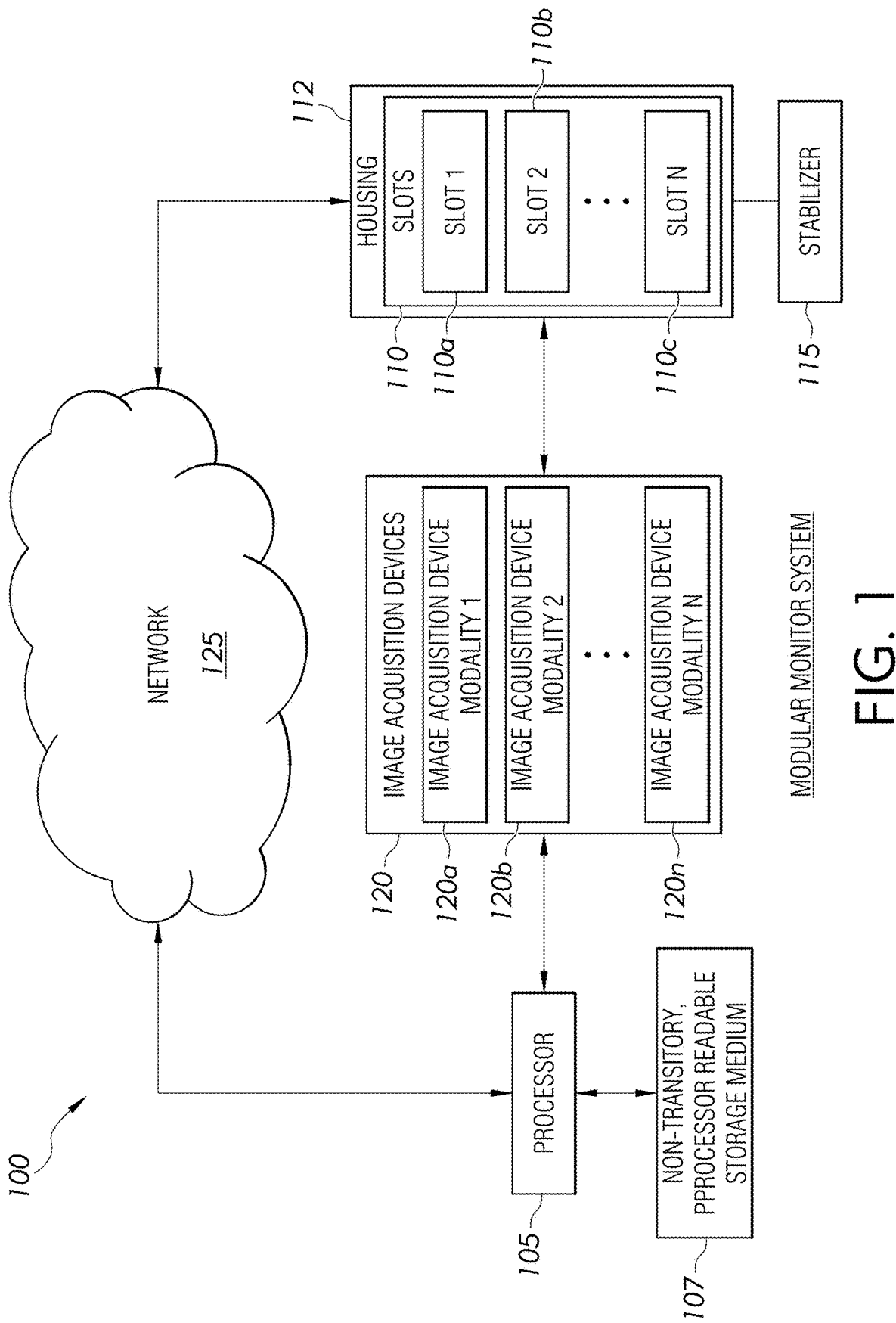
FIG. 1 depicts a schematic diagram of an example modular monitor system, according to one or more embodiments shown and described herein.

The present disclosure relates to systems and methods for modular monitoring, and more particularly, to systems and methods that prioritize and selectively control devices for monitoring objects in a space. In particular, systems and methods disclosed herein provide a modular monitor system that is configured to determine, based on a needed measured or observed clinical condition of a subject, a particular image acquisition device with a given modality. Upon this determination, a specific set of criteria, such as a system computational burden, cost, and imaging modality complexity, may be analyzed to help prioritize which type of image acquisition device should be deployed in response to the clinical condition of the subject. In addition, the modular monitor system is configured to host and control certain image acquisition devices, that are selectively prioritized based on the criteria, received into respective slots, and operated, where overlap of modalities are considered in assessment and addressing different clinical conditions for use cases of a subject. In this manner, the systems and methods disclosed herein are configured to account for overlapping use cases that cross modalities, such as a single use case being addressed by multiple modalities, as well as adjusting modalities to account for real-time changes to the clinical conditions of the subject. By determining, prioritizing, and controlling which modality and image acquisition device is to be selectively deployed and activated, including accounting for updates in real-time subject clinical conditions and deactivating image acquisition devices based on detecting interfering modalities, the system does not need to include all available image acquisition devices, thereby reducing system computational load and increasing system operational efficiency.

While the present disclosure relates particularly to monitoring in a medical setting (e.g., monitoring in medical surgical rooms or the like that include support surfaces or the like), it should be understood that this is merely an example. That is, the systems and methods described herein may be used for or with any type of medical equipment, including, but not limited to, overhead lifts, vital monitoring equipment, control devices, wall-mounted displays, nurses station equipment, surgical equipment, furniture, wheelchairs, and the like. Further, the systems and methods described herein may be used for or with non-medical equipment such as, for example, office equipment such as printers, fax machines, communications equipment, farm equipment, manufacturing equipment, and the like. In addition, while the present disclosure relates specifically to medical facilities such as hospitals, physician offices, urgent care centers, clinics, and the like, it should be understood that this is merely an example. That is, the systems and methods described herein may be located in other locations outside of medical facilities, such as offices, factories, farms, and/or the like.

FIG. 1 depicts a schematic diagram of a modular monitor system 100. The modular monitor system 100 includes a processor 105, a non-transitory, processor readable storage medium 107, a housing 112 that includes plurality of slots 110, a stabilizer 115, a plurality of image acquisition devices 120, and a network 125. Although FIG. 1 illustrates single instances of the constituent components of the modular monitor system 100, the modular monitor system 100 may include any number of constituent components.

The processor 105, such as a central processing unit (CPU), may be the central processing unit that is configured to perform calculations and logic operations to execute one or more programs. The processor 105, alone or in conjunction with the other components, may be an illustrative processing device, computing device, processor, or combinations thereof, including, for example, a multi-core processor, a microcontroller, a field-programmable gate array (FPGA), or an application-specific integrated circuit (ASIC). The processor 105 may include any processing component configured to receive and execute instructions (such as from the non-transitory, processor readable storage medium 107). In some embodiments, the processor 105 may include a plurality of processing devices.

The non-transitory, processor readable storage medium 107 may contain one or more data repositories for storing data that is received and/or generated. The non-transitory, processor readable storage medium 107 may be any physical storage medium, including, but not limited to, a hard disk drive (HDD), memory (e.g., read-only memory (ROM), programmable read-only memory (PROM), random access memory (RAM), double data rate (DDR) RAM, flash memory, and/or the like), removable storage, a configuration file (e.g., text) and/or the like. While the non-transitory, processor readable storage medium 107 is depicted as a local device, it should be understood that the non-transitory, processor readable storage medium 107 may be a remote storage device, such as, for example, a server computing device, cloud-based storage device, or the like. The non-transitory, processor readable storage medium 107 may be communicatively coupled to the processor 105.

The plurality of slots 110, which may be part of a housing 112, such as a housing apparatus or a housing device, may each include a predetermined shape, such as a square, a rectangular, an oval, a triangle, a circle. Alternatively or additionally, the plurality of slots 110 may each include a predetermined quantity that can be equally or differently divided relative to the housing 112. By way of a non-limiting example, the plurality of slots 110 may be integrated with the housing 112 that includes a first slot having a rectangular shape, and a second slot having a triangle shape. By way of another non-limiting example, the plurality of slots 110 may be integrated with the housing 112 that includes four slots, each slot being equally shaped as a quarter of a circle. It is understood that the plurality of slots 110 may take form of any shape, size, and quantity.

In some examples, certain types of modalities, and subsequently, certain types of image acquisition devices 120 including such certain types of modalities, may require a slot 110 having a predetermined size. By way of example, a first image acquisition device 120a including an imaging modality may be configured to be received in a first slot 110, and a second image acquisition device 120b including a non-imaging modality, such as an audio modality, may be configured to be received in a second slot 110, the size of the second slot 110 including a half slot whereas the size of the first slot 110 including a full slot. In this manner, the capacity of the modular monitor system increases for lower modality complexity image acquisition devices 120.

Any of the plurality of slots 110 may be configured to receive the plurality of image acquisition devices 120. For example, any image acquisition device 120 may be inserted into a slot 110. Each slot 110 may include one or more cables (not shown) and/or one or more communication terminals (not shown) that provide power to the image acquisition device 120, allow for the image acquisition device 120 to be recognized when inserted, and/or enable communication between the image acquisition device 120 and the processor 105 so as to enable the image acquisition device 120 to perform in the manner for which it is configured. In some examples, the image acquisition device 120 may be configured to include RFID or wireless proximity provision that allows for identification of a type and class of sensors being placed in any or each slot 110.

The stabilizer 115 may include a gimbal stabilizer that is configured to support and stabilize the modular monitor system 100. In some examples, the stabilizer 115 may be electronically controlled by the processor 105. In other examples, the stabilizer 115 may be mechanically controlled without the processor 105. By way of example, the stabilizer 115 may be connected to the housing 112 that includes the plurality of slots 110. The stabilizer 115 may be connected to an outer surface of the housing 112 at opposite ends and secured by a respective bolt. The stabilizer 115 provides stability to the housing 112 by allowing it to remain at a fixed position without movement interruption. In some examples, the stabilizer 115 restricts movement of the housing 112 relative to a predetermined axis, such as a vertical axis, of the housing 112. In other examples, the stabilizer 115 may be configured to allow for pan and/or tilt of the housing 112. While the stabilizer 115 may be hook-shaped, it is understood that the stabilizer 115 may include any other type of shape.

The plurality of image acquisition devices 120 may be configured to be received in any one of the plurality of slots 110. For example, any of the plurality of image acquisition devices 120 may be configured to be appropriately dimensioned to be received in the plurality of slots 110. In some examples, an image acquisition device 120 may be similarly sized and shaped as the corresponding slot 110 that it loads into. Any image acquisition device 120 may also be modular such that it can be inserted into and removed from a corresponding slot 110. The plurality of image acquisition devices 120 may include a daylight visible camera, an infrared night vision camera, a thermal camera, a point cloud depth camera, or any combination thereof. The daylight visible camera may be configured to capture and image objects in visible light. The infrared night vision camera may be configured to capture and image objects in low light or night light using infrared radiation. The thermal camera may be configured to capture and image objects using thermal radiation. The point cloud depth camera may be configured to capture and image objects by creating a point cloud using a collection of data points that include depth information and color information. The plurality of image acquisition devices 120 may be communicatively coupled with the processor 105. As explained above, the processor 105 may be communicatively coupled to any image acquisition device 120 by wireless communication via one or more communication modules (not shown) of each image acquisition device 120, by serial communication via one or more cables (not shown) located in each slot 110 and that are connected one or more communication terminals also located in each slot 110, or any combination thereof.

In some examples, any of the one or more image acquisition devices 120 that are configured to be received in the plurality of slots 110 may include a different modality. In other examples, any of the one or more image acquisition devices 120 that are configured to be received in the plurality of slots 110 may include a similar modality. Without limitation, the modality may include various types of modalities, such as structured illumination, infrared illumination, and directed radio frequency antenna and power transmission. By way of example, the plurality of image acquisition devices 120 may include a first image acquisition device 120a with a first modality, a second image acquisition device 120b with a second modality, up to and including and a nth image acquisition device 120n with a Nth modality, with n taking a value of any integer that is associated with a particular image acquisition device 120, and N taking a value of any integer that is associated with a modality type of the corresponding image acquisition device 120. Continuing with this example, the first image acquisition device 120a may include a daylight visible camera with a structured illumination modality, and the second image acquisition device 120b may include a thermal camera with an infrared illumination modality.

The network 125 may be one or more of a wireless network, a wired network or any combination of wireless network and wired network and may be configured to connect any of the components of the modular monitor system 100. For example, network 125 may include one or more of a fiber optics network, a passive optical network, a cable network, an Internet network, a satellite network, a wireless local area network (LAN), a Global System for Mobile Communication, a Personal Communication Service, a Personal Area Network, Wireless Application Protocol, Multimedia Messaging Service, Enhanced Messaging Service, Short Message Service, Time Division Multiplexing based systems, Code Division Multiple Access based systems, D-AMPS, Wi-Fi, Fixed Wireless Data, IEEE 802.11b, 802.15.1, 802.11n and 802.11g, Bluetooth, NFC, Radio Frequency Identification (RFID), Wi-Fi, and/or the like.

In addition, network 125 may include, without limitation, telephone lines, fiber optics, IEEE Ethernet 802.3, a wide area network, a wireless personal area network, a LAN, or a global network such as the Internet. In addition, network 125 may support an Internet network, a wireless communication network, a cellular network, or the like, or any combination thereof. Network 125 may further include one network, or any number of the exemplary types of networks mentioned above, operating as a stand-alone network or in cooperation with each other. Network 125 may utilize one or more protocols of one or more network elements to which they are communicatively coupled. Network 125 may translate to or from other protocols to one or more protocols of network devices. Although network 125 is depicted as a single network, it should be appreciated that according to one or more examples, network 125 may include a plurality of interconnected networks, such as, for example, the Internet, a service provider's network, a cable television network, corporate networks, such as credit card association networks, and home networks.

Figure 2:
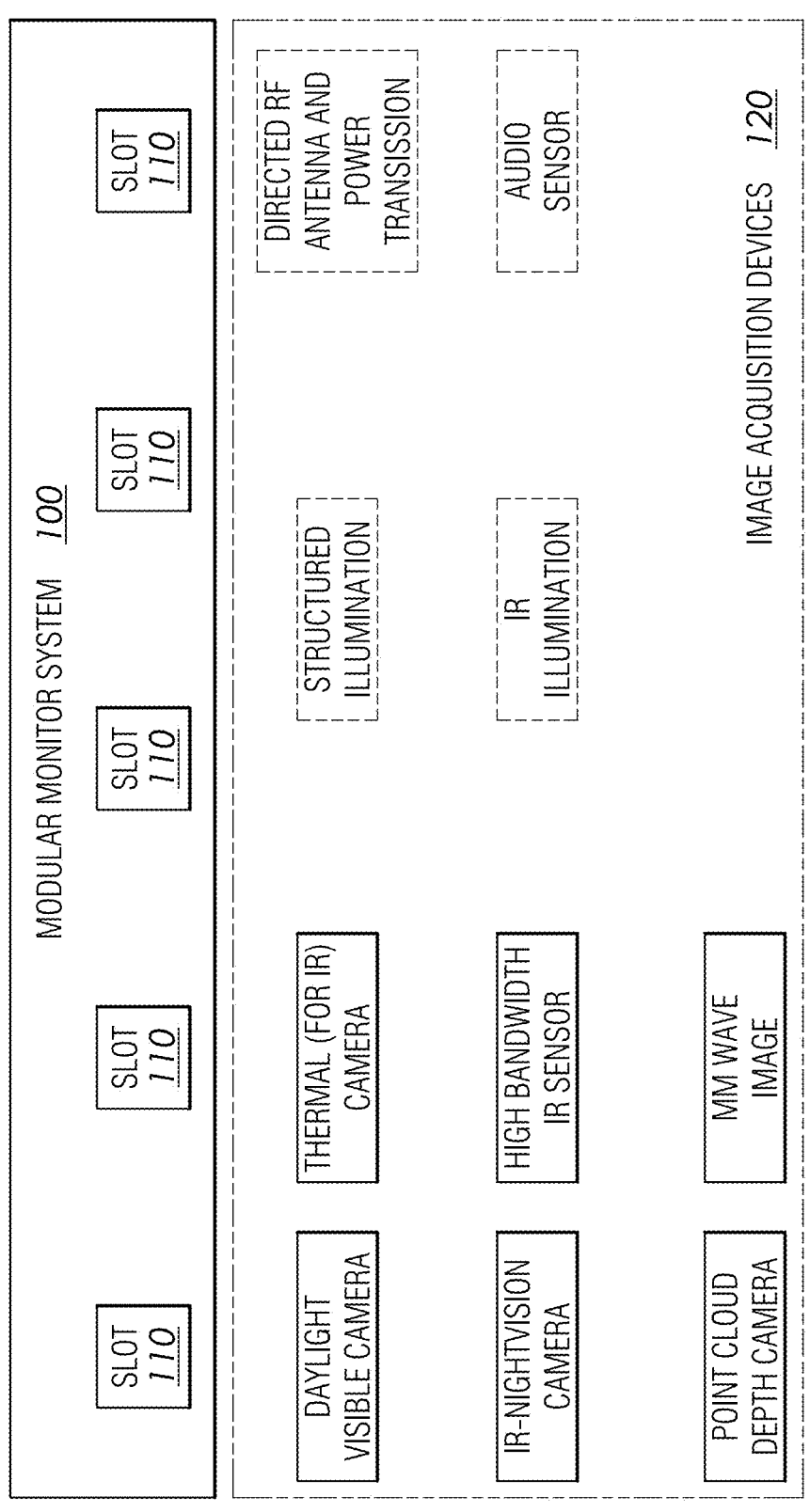
FIG. 2 depicts a schematic diagram of image acquisition device types and modalities of a modular monitor system of FIG. 1, according to one or more embodiments shown and described herein.

FIG. 2 depicts a schematic diagram of image acquisition device types and modalities. Although FIG. 2 illustrates single instances of the constituent components of the image acquisition device types, the modular monitor system 100 may include any number of constituent components. FIG. 2 may reference and incorporate any of the above constituent components and operations of the modular monitor system 100 of FIG. 1. The modular monitor system 100 includes a plurality of slots 110 and a plurality of image acquisition devices 120.

For example, the plurality of image acquisition devices 120 may include a daylight visible camera 120a, an infrared night vision camera 120b, a thermal camera 120c, a point cloud depth camera 120d, a high bandwidth infrared sensor 120e, a millimeter wave imaging sensor 120f, or any combination thereof. The daylight visible camera 120a may be configured to capture and image objects in visible light. The infrared night vision camera 120b may be configured to capture and image objects in low light or night light using infrared radiation. The thermal camera 120c may be configured to capture and image objects using thermal radiation. The point cloud depth camera 120d may be configured to capture and image objects by creating a point cloud using a collection of data points that include depth information and color information. The high bandwidth infrared sensor 120e may be configured to measure infrared radiation relative to an object in a given environment. The millimeter wave imaging sensor 120f may be configured to detect objects using short-wavelength electromagnetic waves. Any of the plurality of image acquisition devices 120 may include a modality, such as structured illumination, infrared illumination, directed radio frequency antenna and power transmission. For example, the modality may include an illumination modality, such as a structured illumination or an IR illumination, and a non-illumination modality, such as directed RF antenna and power transmission or a sound. A modality may have provision configured for steering and focusing its sensed area within an environment, such as pan, tilt, zoom for optical modality or a direction horn antenna for RF modality. In some examples, any of the plurality of image acquisition devices 120 may also include an audio sensor. In some examples, the high bandwidth infrared sensor 120e may comprise a thermal camera or a thermopile.

As further depicted in FIG. 2, a plurality of slots 110 are empty and available, each configured to receive the plurality of image acquisition devices 120, which may each include a different or similar modality. For example, any image acquisition device 120 may be inserted into a slot 110. Any slot 110 may include one or more cables (not shown) and/or one or more communication terminals (not shown) that provide power to the image acquisition device 120, allow for the image acquisition device 120 to be recognized when inserted, and/or enable communication between the image acquisition device 120 and the processor 105 so as to enable the image acquisition device 120 to perform in the manner for which it is configured.

Figure 3:
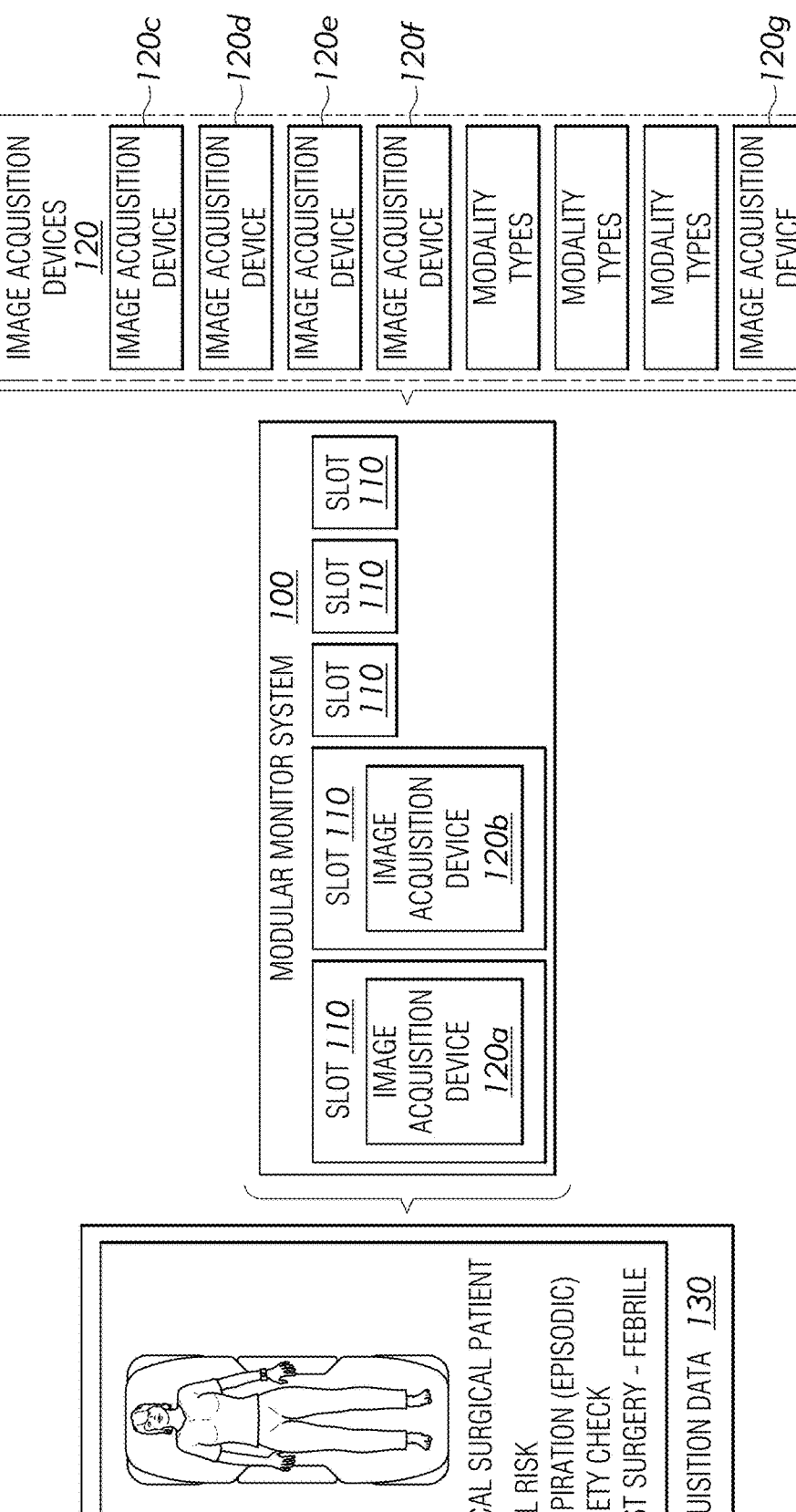
FIG. 3 depicts a schematic diagram of certain image acquisition devices loaded into certain slots of a modular monitor system of FIGS. 1-2, according to one or more embodiments shown and described herein.

FIG. 3 depicts a schematic diagram of certain image acquisition devices loaded into certain slots of a modular monitor system 100. Although FIG. 3 illustrates single instances of the constituent components of the image acquisition device types and slots, the modular monitor system 100 may include any number of constituent components.

FIG. 3 may reference and incorporate any of the above constituent components and operations of the modular monitor system 100 of FIGS. 1-2.

As further depicted in FIG. 3, the plurality of image acquisition devices 120 may include a first image acquisition device 120a, such as a daylight visible camera, and a second image acquisition device 120b, such as a thermal camera. The daylight visible camera may be configured to be received in a first slot of the plurality of slots 110, and the thermal camera may be configured to be received in a second slot of the plurality of slots 110. In some examples, a plurality of remaining slots 110 may be available and configured to receive additional plurality of image acquisition devices 120. As depicted in FIG. 3, three additional remaining slots 110 are indicated as being empty and available, and two slots 110 are occupied and loaded with the first image acquisition device 120a and the second image acquisition device 120b.

Other types of image acquisition devices 120 may be inserted into the plurality of slots 110, and are not limited to the first image acquisition deice 120a and the second image acquisition device 120b. For example, the other types of image acquisition devices 120 may include a third image acquisition device 120c, such as a high bandwidth IR sensor, a fourth image acquisition device 120d, such as a millimeter wave image sensor, a fifth image acquisition device 120e, such as a point cloud depth camera, a sixth image acquisition device 120f, such as an IR nightvision camera, and a seventh image acquisition device 120g, such as an audio sensor.

The acquisition data 130 may be data that is acquired by the processor 105. In some examples, the acquisition data 130 may be associated with a subject, and include subject fall risk data, subject respiration data, subject febrile data, subject safety check data, subject symptom data, subject post-surgical data in a given environment, or any combination thereof, any of which may be obtained in real-time by the processor 105. For example, the processor 105 may be configured to acquire, via one or more algorithms, the acquisition data 130 from any number of the plurality of image acquisition devices 120. The acquisition data 130 may include the above-identified data that is evidentiary of, or indicative of, one or more conditions of the subject in a given environment. In some examples, the one or more algorithms may be configured to implement machine learning object identification, classification, and location to feed a mechanical state machine that is configured to determine the one or more conditions, in real-time, of the subject.

Figure 4:
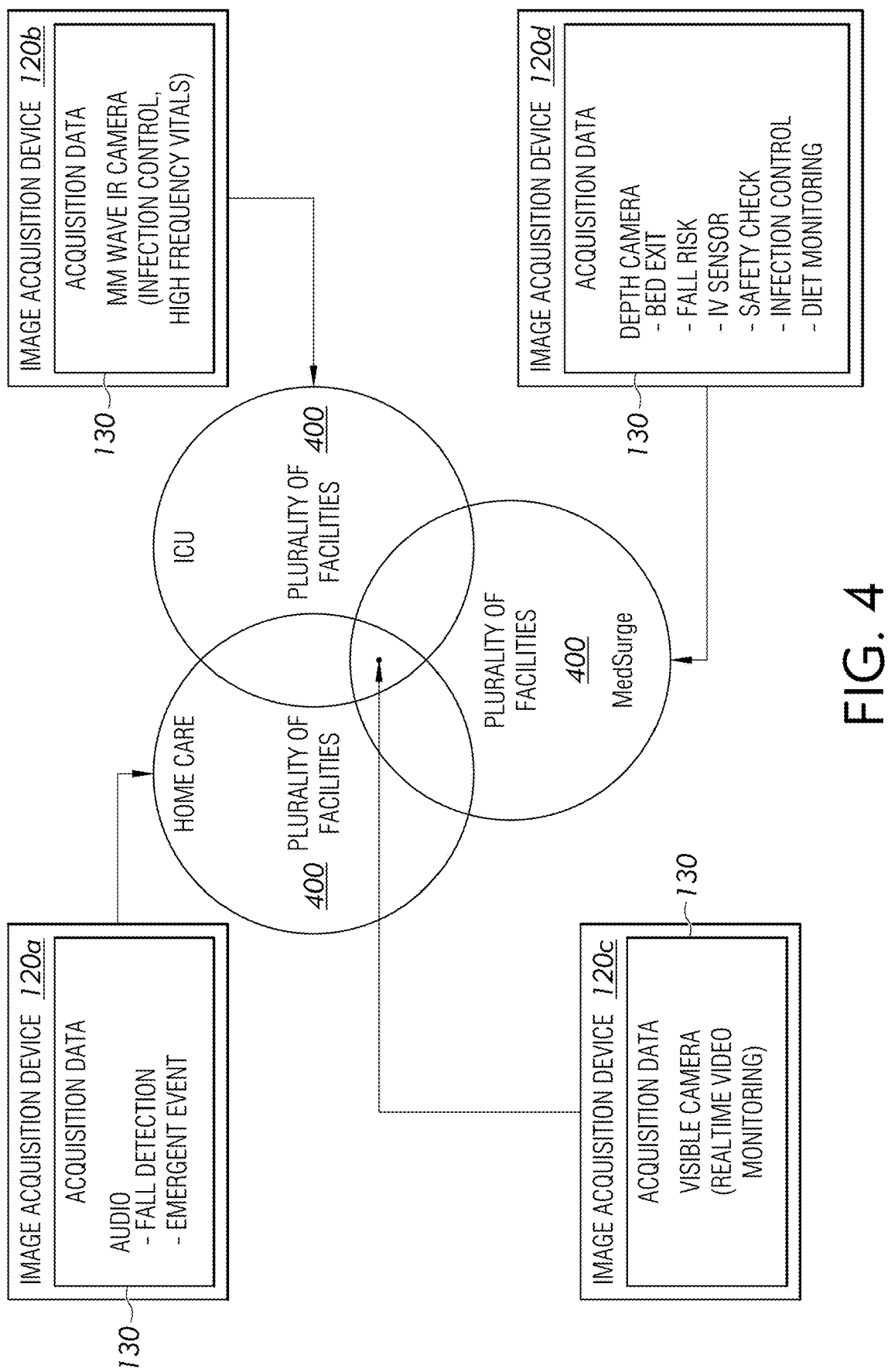
FIG. 4 depicts a schematic diagram of a plurality of facilities and a plurality of image acquisition devices of FIGS. 1-3, according to one or more embodiments shown and described herein.

FIG. 4 depicts a schematic diagram of a plurality of facilities 400 and a plurality of image acquisition devices 120. Although FIG. 4 illustrates single instances of the constituent components of the image acquisition device types, the modular monitor system 100 may include any number of constituent components. FIG. 4 may reference and incorporate any of the above constituent components and operations of the modular monitor system 100 of FIGS. 1-3.

Without limitation, the plurality of facilities 400 may include a home care facility, a medical-surgical ("med-surg") facility, an intensive care unit (ICU), an assisted care facility, a hospital, a nursing home, and the like. The plurality of facilities 400 may be depicted as part of a Venn diagram, and different image acquisition devices 120 may be configured to dynamically asses clinical conditions and desired use cases, as further explained below.

For example, a first image acquisition device 120a may include an audio sensor for a facility 400 (e.g., a home care facility), in which acquisition data 130 includes fall detection data, emergency event data, or any combination thereof, for a first use case. A second image acquisition device 120b may include a millimeter wave infrared camera for the ICU facility, in which acquisition data 130 includes infection control data, high frequency vitals data, or any combination thereof, for a second use case. A third image acquisition device 120c may include a visible camera for an overlap between various facilities 400 (e.g., as noted above, a home care facility, an ICU facility, a med-surg facility, or the like) for a third use case. In particular, the visible camera may be used for not only one of the facilities 400, but for a portion of use cases that overlap between the plurality of facilities 400. A fourth image acquisition device 120d may include a depth camera for a facility 400 (e.g., a med-surg facility), in which acquisition data 130 includes bed exit data, fall risk data, IV sensor data, safety check data, infection control data, diet monitoring data, or any combination thereof, for a fourth use case. It should be understood that each of the image acquisition devices 120a-120d are not limited to these particular image acquisition devices 120, and that other types of image acquisition devices 120 may instead be used.

Figure 5B:
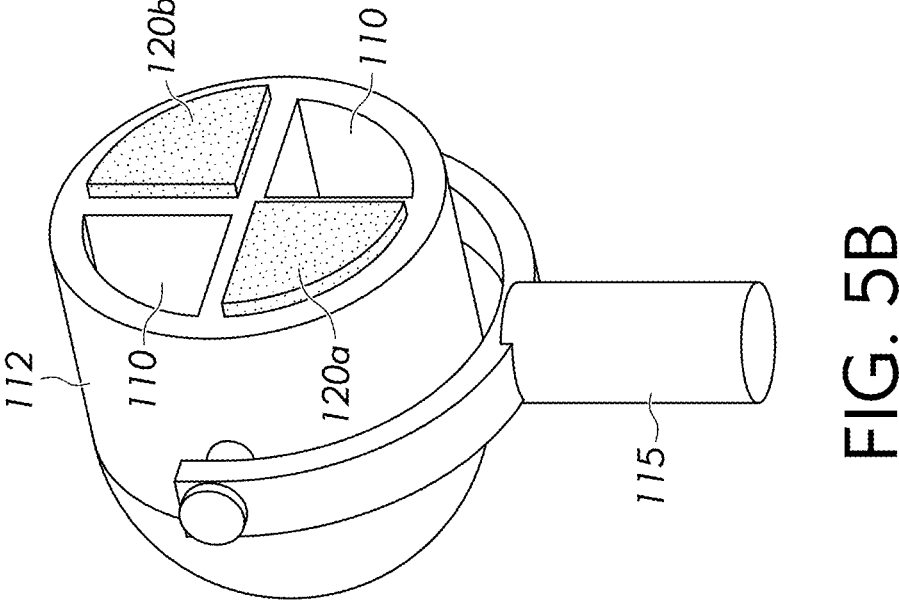
FIG. 5B depicts a perspective view of the portion of the modular monitor system of FIG. 5A, according to one or more embodiments shown and described herein.
Figure 5A:
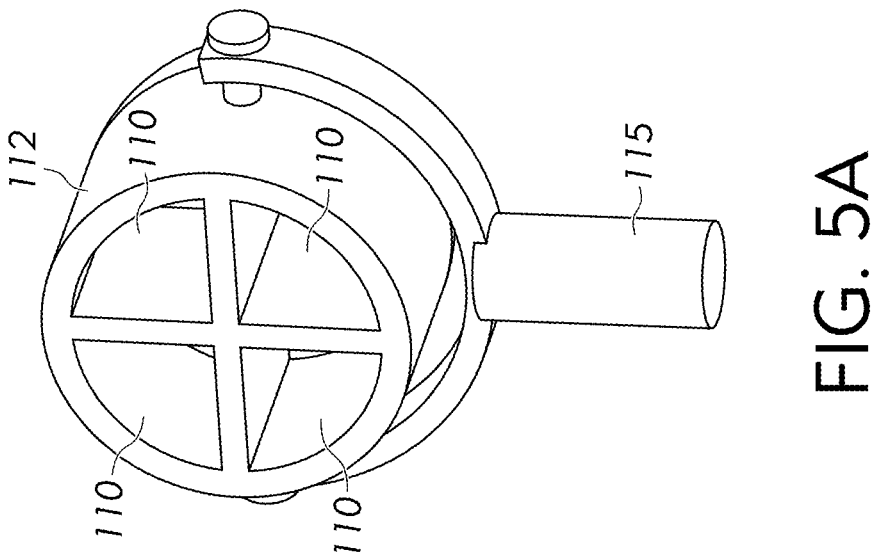
FIG. 5A depicts a perspective view of a portion of a modular monitor system that includes a housing including a plurality of slots and a stabilizer of FIG. 1, according to one or more embodiments shown and described herein.

FIGS. 5A-5B depict a perspective view of a portion of a modular monitor system 100 that includes a housing 112 including a plurality of slots 110 and a stabilizer 115. Although FIGS. 5A-5B illustrate single instances of the constituent components of the housing 112 and the stabilizer 115, the housing 112 and the stabilizer may include any number of constituent components. FIGS. 5A-5B may reference and incorporate any of the above constituent components and operations of the modular monitor system 100 of FIGS. 1-4.

As depicted in FIG. 5A, the plurality of slots 110 of the housing 112 are empty and available and configured to receive a plurality of image acquisition devices 120. FIG. 5B depicts a plurality of slots 110 in which two of a plurality of image acquisition devices 120 respectively occupy a corresponding slot of the plurality of slots 110. In both FIGS. 5A-5B, a stabilizer 115 is depicted and configured to support and stabilize the plurality of image acquisition devices 120 that are configured to be received in the plurality of slots 110.

Turning to FIG. 5B, and by way of example, a first image acquisition device 120a may include a point cloud depth camera configured in a bottom corner portion corresponding to a first slot 110 of the housing 112, and a second image acquisition device 120b may include a millimeter wave infrared camera in an upper corner portion corresponding to a second slot 110 of the housing 112. The housing 112 may include the plurality of slots 110 connected to the stabilizer 115.

Any of the plurality of image acquisition devices 120 may be configured to be removed from the plurality of slots 110, or received into the plurality of slots 110 without interrupting a power supply or operation of the remaining plurality of image acquisition devices 120. In some examples, the plurality of image acquisition devices 120 may be configured to operate independently and separately of each other once they are configured to be received in the plurality of slots 110. In other examples, the plurality of image acquisition devices 120 may be configured to operate collectively with one or more other image acquisition devices 120.

Figure 6:
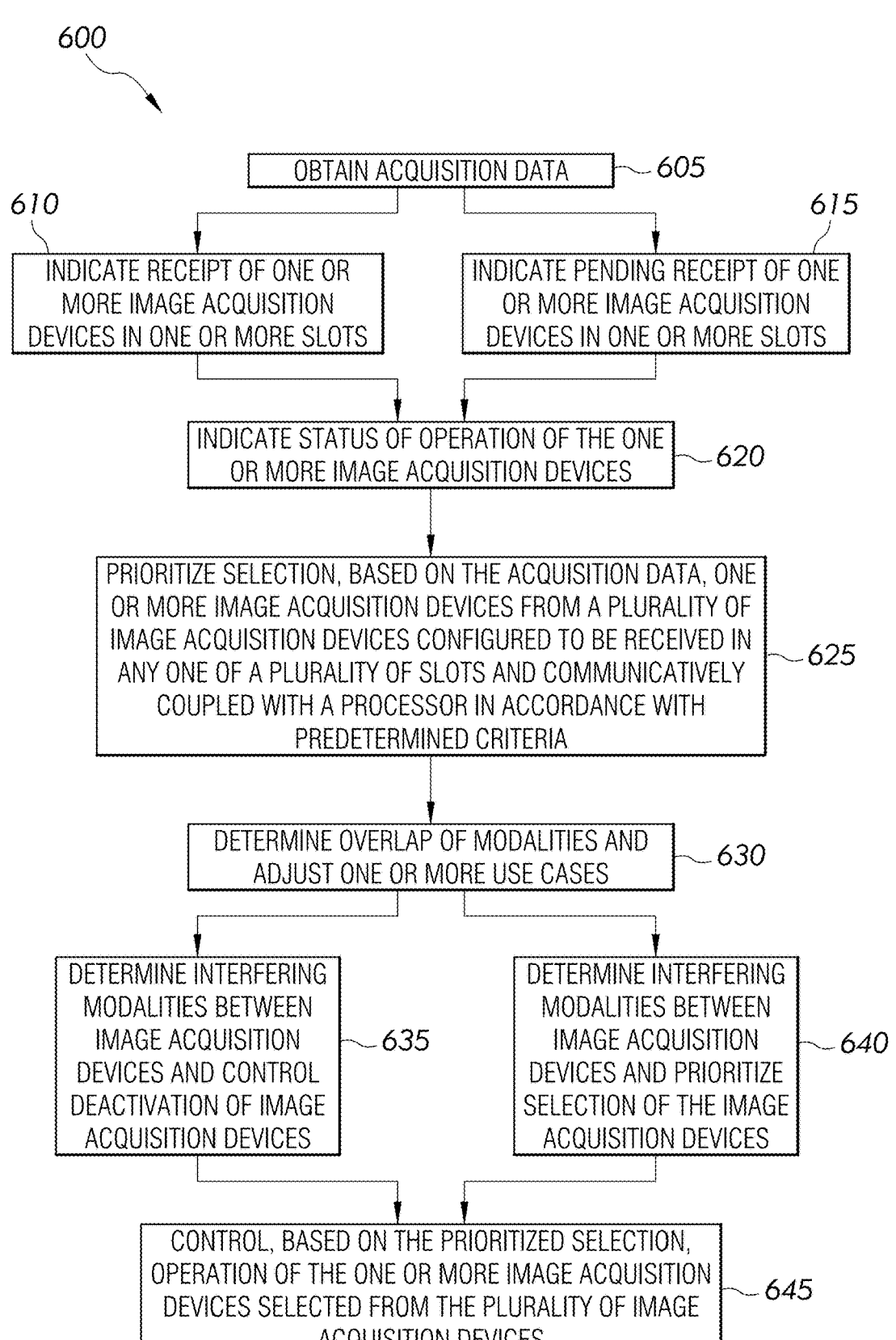
FIG. 6 depicts a flow diagram of an example method to be performed by the modular monitor system of FIGS. 1-5.

FIG. 6 depicts a flow diagram of an example method 600 to be performed by the modular monitor system of FIGS. 1-5. The method 600 may include prioritizing and selectively controlling image acquisition devices 120 for monitoring objects in a space. FIG. 6 may reference and incorporate any of the above constituent components and operations of the modular monitor system 100 of FIGS. 1-5A and 5B. As explained above, the modular monitor system 100 may include a processor 106 that is communicatively coupled to a non-transitory, processor readable storage medium 107.

At block 605, the non-transitory, processor readable storage medium 107 may include one or more instructions stored thereon that, when executed, cause the processor 105 to obtain acquisition data. In some examples, the acquisition data includes subject fall risk data, subject respiration data, subject febrile data, subject safety check data, subject symptom data, subject post-surgical data, or any combination thereof, any of which may be obtained in real-time by the processor 105. For example, the processor 105 may be configured to obtain the acquisition data from the plurality of image acquisition devices 120.

At block 610, in some examples, the non-transitory, processor readable storage medium 107 may include one or more instructions stored thereon that, when executed, cause the processor 105 indicate the one or more image acquisition devices 120 that are actually received in any one of the plurality of slots 110. At block 615, in other examples, the non-transitory, processor readable storage medium 107 may include one or more instructions stored thereon that, when executed, cause the processor 105 to indicate the one or more image acquisition devices 120 that are to be received in any one of the plurality of slots 110. In some examples, the indication regarding actual receipt of the image acquisition device 120 into a slot 110, or the indication regarding pending receipt of the image acquisition device 120 into a slot 110, may be displayed via an identification indicator, such as a light emitting diode (not shown), located at an opening of the slot.

For example, an image acquisition device 120 may be inserted into a slot 110. A slot 110 may include one or more cables (not shown) and/or one or more communication terminals (not shown) that provide power to the image acquisition device 120, allow for the image acquisition device 120 to be recognized when inserted, and/or enable communication between the image acquisition device 120 and the processor 105 so as to enable the image acquisition device 120 to perform in the manner for which it is configured.

At block 620, the non-transitory, processor readable storage medium 107 may include one or more instructions stored thereon that, when executed, cause the processor 105 to indicate a status of operation of the one or more image acquisition devices 120 selected from plurality of image acquisition devices 120. Any of the image acquisition devices 120 may be associated with the identification indicator that is located at a respective opening of the plurality of slots 110. For example, the identification indicator may include an alphanumeric indicator that indicates, to the processor 105, a particular image acquisition device 120 that is (or needs to be) received in a particular slot 110, as well as a status of operation. The status of operation may indicate whether the particular image acquisition device 120 is received in the particular slot 110, whether the particular image acquisition device 120 is powered on, whether the particular image acquisition device 120 is performing an operation, whether the particular image acquisition device 120 is in sleep or standby mode, or whether the particular image acquisition device 120 is powered off. In this manner, the processor 105 determines what types of modalities, and subsequently, what types of image acquisition devices 120 including such types of modalities should be deployed.

In some examples, the non-transitory, processor readable storage medium 107 may include one or more instructions stored thereon that, when executed, cause the processor 105 to separately activate and deactivate the plurality of image acquisition devices 120. For example, the plurality of image acquisition devices 120 may be individually powered on and powered off by the processor 105. In other examples, the non-transitory, processor readable storage medium 107 may include one or more instructions stored thereon that, when executed, cause the processor 105 to collectively activate and deactivate the plurality of image acquisition devices 120. For example, the plurality of image acquisition devices 120 may be collectively powered on and powered off by the processor 105.

At block 625, the non-transitory, processor readable storage medium 107 may include one or more instructions stored thereon that, when executed, cause the processor 105 to prioritize selection, based on the acquisition data, of one or more image acquisition devices 120 from the plurality of image acquisition devices 120 in accordance with predetermined criteria. The predetermined criteria may include a computational load, image acquisition device 120 availability, image acquisition device 120 cost, one or more use cases, or any combination thereof. By way of example, vital signs of a subject (including but not limited to subject body temperature, subject pulse rate, subject respiration rate, subject blood pressure) may be captured by an image acquisition device 120 that includes a visible camera; fall risk and pose estimation of the subject may be captured by an image acquisition device 120 that includes a depth camera; and fever of the subject may be captured by an image acquisition device 120 that includes a thermal or IR camera.

In some examples, certain types of modalities, and subsequently, certain types of image acquisition devices 120 including such certain types of modalities, may require a slot 110 having a predetermined size. By way of example, a first image acquisition device 120a including an imaging modality may be configured to be received in a first slot 110, and a second image acquisition device 120b including a non-imaging modality, such as an audio modality, may be configured to be received in a second slot 110, the size of the second slot 110 including a half slot whereas the size of the first slot 110 including a full slot. In this manner, the capacity of the modular monitor system increases for lower modality complexity image acquisition devices 120.

Based on the real-time condition of the subject, any of the modalities of the plurality of image acquisition devices 120 may be appropriately updated to account for the symptoms or behaviors exhibited by the subject.

In some examples, any of plurality of image acquisition devices 120 may be configured to include one or more imaging modalities and one or more illumination modalities. For example, the one or more illumination modalities may be configured to emanate a predetermined type and/or amount of light, radiofrequency energy, and audio sensing. In some examples, during an image acquisition cycle for oxygen saturation (SpO2), an image acquisition device 120 may be configured to flash a desired color light (such as a green light) of frequency where oxygenated hemoglobin is known to have a maximal return signal, or infrared signal for where de-oxygenated hemoglobin is known to demonstrate. The processor 105 may be configured to instruct the image acquisition device to flash the desired light of frequency.

At block 630, the non-transitory, processor readable storage medium 107 may include one or more instructions stored thereon that, when executed, cause the processor 105 to determine an overlap of modalities between respective ones of the one or more image acquisition devices 120 selected from the plurality of image acquisition devices 120. The non-transitory, processor readable storage medium 107 may include one or more instructions stored thereon that, when executed, cause the processor 105 to dynamically adjust the one or more use cases based on the overlap of modalities.

At block 635, in some examples, the non-transitory, processor readable storage medium 107 may include one or more instructions stored thereon that, when executed, cause the processor 105 to determine interfering modalities between respective ones of the one or more image acquisition devices 120 selected from the plurality of image acquisition devices 120. For example, to the extent a first image acquisition device 120a includes a first modality that interferes, such as via noise interference during operation of a second image acquisition device 120b that includes a second modality, the processor 105 may be configured to control operation of either of the first image acquisition device 120a or the second image acquisition device 120b to prevent operation interference due to the other image acquisition device 120. The non-transitory, processor readable storage medium 107 may include one or more instructions stored thereon that, when executed, cause the processor 105 to control deactivation of the one or more image acquisition devices 120 selected from the plurality of image acquisition devices 120 based on the interfering modalities. The processor 105 may be configured to interleave and prioritize the modality selection using an a-priori map of the one or more clinical conditions of the subject. By way of example, a stroke may be weighted more important than febrile, such prioritization of a modality selection corresponding to this particular condition of the subject may be performed more frequently than other clinical conditions of the subject. The processor 105 may be configured to generate a scheduling operation algorithm that is configured to utilize clinical rules of deterioration in conjunction with an observed subject status. For example, the type of disease or recovery that the subject is presently undergoing may cause the processor 105 to prioritize those modalities that are responsible for or corresponding to the type of disease or recovery.

At block 640, in some examples, the non-transitory, processor readable storage medium 107 may include one or more instructions stored thereon that, when executed, cause the processor 105 to determine interfering modalities between respective ones of the one or more image acquisition devices 120 selected from the plurality of image acquisition devices 120. For example, to the extent a first image acquisition device 120a includes a first modality that interferes, such as via noise interference during operation of a second image acquisition device 120b that includes a second modality, the processor 105 may be configured to control operation of either of the first image acquisition device 120a or the second image acquisition device 120b to prevent operation interference due to the other image acquisition device 120. The non-transitory, processor readable storage medium 107 may include one or more instructions stored thereon that, when executed, cause the processor 105 to prioritize selection of the one or more image acquisition devices 120 selected from the plurality of image acquisition devices 120 based on the interfering modalities.

At block 645, the non-transitory, processor readable storage medium 107 may include one or more instructions stored thereon that, when executed, cause the processor 105 to control, based on the prioritized selection, operation of the one or more image acquisition devices 120 selected from the plurality of image acquisition devices 120.

As a non-limiting example of the systems and methods described above, a tidal volume of a subject may need to be acquired and monitored. This may be due to, for example, the subject experiencing lung problems and/or breathing issues, thereby defining a first use case. The processor 105 is configured to instruct lighting of an indicator located at an opening of a slot 110 that is configured to receive a depth camera with a given modality relative to the first use case. The processor 105 is configured to cause the indicator to intermittently flash and/or sound, for example for a predetermined time duration, until receipt of the depth camera in the slot 110. Upon receipt of the depth camera in the slot 110, the processor 105 may be configured to acquire a tidal volume measurement of the subject for the first use case.

Continuing with the above example, the processor 105 may be configured to determine which alternative and/or additional modalities (and subsequently, which corresponding image acquisition devices 120) are needed, or need to be updated, for receipt in a given slot 110, based on observed or changed clinical conditions, in real-time, of the subject.

As another non-limiting example of the systems and methods described above, a medical room including a subject, but no nurse or doctor, may need to be monitored for thermal imaging purposes. The processor 105 may be configured to determine that an image acquisition device 120 including a thermal imaging modality is needed to be received in a slot 110. Based on this determination, the processor 105 may be configured to instruct lighting of an indicator located at an opening of a slot 110 that is configured to receive the image acquisition device 120 including the thermal imaging modality. The processor 105 is configured to cause the indicator to intermittently flash and/or sound, for example for a predetermined time duration, until receipt of the image acquisition device 120 including the thermal imaging modality in the slot 110. Upon receipt of the image acquisition device 120 including the thermal imaging modality in the slot 110, the processor 105 may be configured to acquire a thermal measurement of the subject. Any indicator, located at a respective opening of a plurality of slots 110, may be instructed to be illuminated by the processor 105 to indicate an availability for receipt of an image acquisition device 120, as well as whether other image acquisition devices 120 are powered on, whether the other image acquisition devices 120 are performing an operation, whether the other image acquisition devices 120 are in sleep or standby mode, or whether other image acquisition devices 120 are powered off.

The present disclosure relates to systems and methods for modular monitoring, and more particularly, to systems and methods that prioritize and selectively control devices for monitoring objects in a space. In particular, systems and methods disclosed herein provide a modular monitor system that is configured to determine, based on a needed measured or observed clinical condition of a subject, a particular image acquisition device with a given modality. Upon this determination, a specific set of criteria, such as a system computational burden, cost, and imaging modality complexity, may be analyzed to help prioritize which type of image acquisition device should be deployed in response to the clinical condition of the subject. Moreover, the modular monitor system is configured to host and control certain image acquisition devices, that are selectively prioritized based on the criteria, received into respective slots, and operated, where overlap of modalities are considered in assessment and addressing different clinical conditions for use cases of a subject. In this manner, the systems and methods disclosed herein are configured to account for overlapping use cases that cross modalities, such as a single use case being addressed by multiple modalities, as well as adjusting modalities to account for real-time changes to the clinical conditions of the subject. By determining, prioritizing, and controlling which modality and image acquisition device is to be selectively deployed and activated, including accounting for updates in real-time subject clinical conditions and deactivating image acquisition devices based on detecting interfering modalities, the system does not need to include all available image acquisition devices, thereby reducing system computational load and increasing system operational efficiency.

Further aspects of the invention are provided by the subject matter of the following clauses.

An modular monitor system, including: a processor; a plurality of slots that each include a predetermined shape; a plurality of image acquisition devices configured to be received in any one of the plurality of slots and communicatively coupled with the processor; and a non-transitory, processor readable storage medium communicatively coupled to the processor, the non-transitory, processor readable storage medium including one or more instructions stored thereon that, when executed, cause the processor to: obtain acquisition data; prioritize selection, based on the acquisition data, of one or more image acquisition devices from the plurality of image acquisition devices in accordance with predetermined criteria, the predetermined criteria including a computational load, image acquisition device availability, image acquisition device cost, one or more use cases, or any combination thereof, the respective ones of the one or more image acquisition devices including a different modality; and control, based on the prioritized selection, operation of the one or more image acquisition devices selected from the plurality of image acquisition devices.

The modular monitor system of any preceding clause, wherein the one or more instructions further cause the processor to indicate the one or more image acquisition devices that are received in any one of the plurality of slots.

The modular monitor system of any preceding clause, wherein the one or more instructions further cause the processor to indicate the one or more image acquisition devices that are to be received in any one of the plurality of slots.

The modular monitor system of any preceding clause, wherein the one or more instructions further cause the processor to indicate a status of operation of the one or more image acquisition devices selected from plurality of image acquisition devices.

The modular monitor system of any preceding clause, wherein the one or more image acquisition devices include a daylight visible camera, an infrared night vision camera, a thermal camera, or a point cloud depth camera.

The modular monitor system of any preceding clause, wherein the acquisition data includes subject fall risk data, subject respiration data, subject febrile data, subject safety check data, subject symptom data, or subject post-surgical data.

The modular monitor system of any preceding clause, further including a gimbal stabilizer configured to support the modular monitor system.

The modular monitor system of any preceding clause, wherein the one or more instructions further cause the processor to: determine an overlap of modalities between of the respective ones of the one or more image acquisition devices selected from the plurality of image acquisition devices; and dynamically adjust the one or more use cases based on the overlap of modalities.

The monitor system of any preceding clause, wherein the one or more instructions further cause the processor to: determine interfering modalities between of the respective ones of the one or more image acquisition devices selected from the plurality of image acquisition devices; and control deactivation of the respective ones of the one or more image acquisition devices selected from the plurality of image acquisition devices based on the interfering modalities.

The modular monitor system of any preceding clause, wherein the one or more instructions further cause the processor to: determine interfering modalities between the respective ones of the one or more image acquisition devices selected from the plurality of image acquisition devices; and prioritize selection of the respective ones of the one or more image acquisition devices selected from the plurality of image acquisition devices based on the interfering modalities.

A method, including: obtaining acquisition data; prioritizing selection, based on the acquisition data, of one or more image acquisition devices from a plurality of image acquisition devices in accordance with predetermined criteria, the predetermined criteria including a computational load, image acquisition device availability, image acquisition device cost, one or more use cases, or any combination thereof, the plurality of image acquisition devices configured to be received in any one of a plurality of slots that each include a predetermined shape, of the respective ones of the one or more image acquisition devices including a different modality; and controlling, based on the prioritized selection, operation of the one or more image acquisition devices selected from the plurality of image acquisition devices.

The method of any preceding clause, further including indicating the one or more image acquisition devices that are received in any one of the plurality of slots.

The method of any preceding clause, further including indicating the one or more image acquisition devices that are to be received in any one of the plurality of slots.

The method of any preceding clause, further including indicating a status of operation of the one or more image acquisition devices selected from the plurality of image acquisition devices.

The method of any preceding clause, wherein the one or more image acquisition devices include a daylight visible camera, an infrared night vision camera, a thermal camera, or a point cloud depth camera.

The method of any preceding clause, wherein the acquisition data includes subject fall risk data, subject respiration data, subject febrile data, subject safety check data, subject symptom data, or subject post-surgical data.

The method of any preceding clause, further including determining an overlap of modalities between the respective ones of the one or more image acquisition devices selected from the plurality of image acquisition devices; and dynamically adjusting the one or more use cases based on the overlap of modalities.

The method of any preceding clause, further including determining interfering modalities between of the respective ones of the one or more image acquisition devices selected from the plurality of image acquisition devices; and controlling deactivation of the respective ones of the one or more image acquisition devices selected from the plurality of image acquisition devices based on the interfering modalities.

The method of any preceding clause, further including determining interfering modalities between the respective ones of the one or more image acquisition devices selected from the plurality of image acquisition devices; and prioritizing selection of the respective ones of the one or more image acquisition devices selected from the plurality of image acquisition devices based on the interfering modalities.

A non-transitory, computer-readable medium including instructions that, when executed by at least one processor, cause the at least one processor to perform one or more operations including: obtaining acquisition data; prioritizing selection, based on the acquisition data, of one or more image acquisition devices from a plurality of image acquisition devices in accordance with predetermined criteria, the predetermined criteria including a computational load, image acquisition device availability, image acquisition device cost, one or more use cases, or any combination thereof, the plurality of image acquisition devices configured to be received in any one of a plurality of slots that each include a predetermined shape, the respective ones of the one or more image acquisition devices including a different modality; and controlling, based on the prioritized selection, operation of the one or more image acquisition devices selected from the plurality of image acquisition devices.

The non-transitory, computer-readable medium of any preceding clause, the one or more operations further including indicating the one or more image acquisition devices that are received in any one of the plurality of slots.

The non-transitory, computer-readable medium of any preceding clause, the one or more operations further including indicating the one or more image acquisition devices that are to be received in any one of the plurality of slots.

The non-transitory, computer-readable medium of any preceding clause, the one or more operations further including indicating a status of operation of the one or more image acquisition devices selected from the plurality of image acquisition devices.

The non-transitory, computer-readable medium of any preceding clause, wherein the one or more image acquisition devices include a daylight visible camera, an infrared night vision camera, a thermal camera, or a point cloud depth camera.

The non-transitory, computer-readable medium of any preceding clause, wherein the acquisition data includes subject fall risk data, subject respiration data, subject febrile data, subject safety check data, subject symptom data, or subject post-surgical data.

The non-transitory, computer-readable medium of any preceding clause, the one or more operations further including: determining an overlap of modalities between the respective ones of the one or more image acquisition devices selected from the plurality of image acquisition devices; and dynamically adjusting the one or more use cases based on the overlap of modalities.

The non-transitory, computer-readable medium of any preceding clause, the one or more operations further including: determining interfering modalities between the respective ones of the one or more image acquisition devices selected from the plurality of image acquisition devices; and controlling deactivation of the respective ones of the one or more image acquisition devices selected from the plurality of image acquisition devices based on the interfering modalities.

The non-transitory, computer-readable medium of any preceding clause, the one or more operations further including: determining interfering modalities between respective ones of the one or more image acquisition devices selected from the plurality of image acquisition devices; and prioritizing selection of the respective ones of the one or more image acquisition devices selected from the plurality of image acquisition devices based on the interfering modalities.

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c). Reference to an element in the singular is not intended to mean only one unless specifically so stated, but rather "one or more." For example, reference to an element (e.g., "a processor," "a memory," etc.), unless otherwise specifically stated, should be understood to refer to one or more elements (e.g., "one or more processors," "one or more memories," etc.). The terms "set" and "group" are intended to include one or more elements, and may be used interchangeably with "one or more." Where reference is made to one or more elements performing functions (e.g., steps of a method), one element may perform all functions, or more than one element may collectively perform the functions. When more than one element collectively performs the functions, each function need not be performed by each of those elements (e.g., different functions may be performed by different elements) and/or each function need not be performed in whole by only one element (e.g., different elements may perform different sub-functions of a function). Similarly, where reference is made to one or more elements configured to cause another element (e.g., an apparatus) to perform functions, one element may be configured to cause the other element to perform all functions, or more than one element may collectively be configured to cause the other element to perform the functions. Unless specifically stated otherwise, the term "some" refers to one or more.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein include one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A modular monitor system, comprising:
a processor;
a plurality of slots that each comprise a predetermined shape;
a plurality of image acquisition devices configured to be received in any one of the plurality of slots and communicatively coupled with the processor; and
a non-transitory, processor readable storage medium communicatively coupled to the processor, the non-transitory, processor readable storage medium comprising one or more instructions stored thereon that, when executed, cause the processor to:
obtain acquisition data;
prioritize selection, based on the acquisition data, of one or more image acquisition devices from the plurality of image acquisition devices in accordance with predetermined criteria, the predetermined criteria including a computational load, image acquisition device availability, image acquisition device cost, one or more use cases, or any combination thereof, the respective ones of the one or more image acquisition devices including a different modality; and control, based on the prioritized selection, operation of the one or more image acquisition devices selected from the plurality of image acquisition devices.

2. The modular monitor system of claim 1, wherein the one or more instructions further cause the processor to indicate the one or more image acquisition devices that are received in any one of the plurality of slots.

3. The modular monitor system of claim 1, wherein the one or more instructions further cause the processor to indicate the one or more image acquisition devices that are to be received in any one of the plurality of slots.

4. The modular monitor system of claim 1, wherein the one or more instructions further cause the processor to indicate a status of operation of the one or more image acquisition devices selected from plurality of image acquisition devices.

5. The modular monitor system of claim 1, wherein the one or more image acquisition devices include a daylight visible camera, an infrared night vision camera, a thermal camera, or a point cloud depth camera.

6. The modular monitor system of claim 1, wherein the acquisition data includes subject fall risk data, subject respiration data, subject febrile data, subject safety check data, subject symptom data, or subject post-surgical data.

7. The modular monitor system of claim 1, further comprising a gimbal stabilizer configured to support the modular monitor system.

8. The modulator monitor system of claim 1, wherein the one or more instructions further cause the processor to:

determine an overlap of modalities between the respective ones of the one or more image acquisition devices selected from the plurality of image acquisition devices; and dynamically adjust the one or more use cases based on the overlap of modalities.

9. The modular monitor system of claim 1, wherein the one or more instructions further cause the processor to:

determine interfering modalities between the respective ones of the one or more image acquisition devices selected from the plurality of image acquisition devices; and control deactivation of the respective ones of the one or more image acquisition devices selected from the plurality of image acquisition devices based on the interfering modalities.

10. The modular monitor system of claim 1, wherein the one or more instructions further cause the processor to:

determine interfering modalities between the respective ones of the one or more image acquisition devices selected from the plurality of image acquisition devices; and prioritize selection of the respective ones of the one or more image acquisition devices selected from the plurality of image acquisition devices based on the interfering modalities.

11. A method, comprising:

obtaining acquisition data;

prioritizing selection, based on the acquisition data, of one or more image acquisition devices from a plurality of image acquisition devices in accordance with predetermined criteria, the predetermined criteria including a computational load, image acquisition device availability, image acquisition device cost, one or more use cases, or any combination thereof, the plurality of image acquisition devices configured to be received in any one of a plurality of slots that each comprise a predetermined shape, the respective ones of the one or more image acquisition devices including a different modality; and controlling, based on the prioritized selection, operation of the one or more image acquisition devices selected from the plurality of image acquisition devices.

12. The method of claim 11, further comprising indicating the one or more image acquisition devices that are received in any one of the plurality of slots.

13. The method of claim 11, further comprising indicating the one or more image acquisition devices that are to be received in any one of the plurality of slots.

14. The method of claim 11, further comprising indicating a status of operation of the one or more image acquisition devices selected from the plurality of image acquisition devices.

15. The method of claim 11, wherein the one or more image acquisition devices include a daylight visible camera, an infrared night vision camera, a thermal camera, or a point cloud depth camera.

16. The method of claim 11, wherein the acquisition data includes subject fall risk data, subject respiration data, subject febrile data, subject safety check data, subject symptom data, or subject post-surgical data.

17. The method of claim 11, further comprising:

determining an overlap of modalities between the respective ones of the one or more image acquisition devices selected from the plurality of image acquisition devices; and dynamically adjusting the one or more use cases based on the overlap of modalities.

18. The method of claim 11, further comprising:

determining interfering modalities between the respective ones of the one or more image acquisition devices selected from the plurality of image acquisition devices; and controlling deactivation of the respective ones of the one or more image acquisition devices selected from the plurality of image acquisition devices based on the interfering modalities.

19. The method of claim 11, further comprising:

determining interfering modalities between the respective ones of the one or more image acquisition devices selected from the plurality of image acquisition devices; and prioritizing selection of the respective ones of the one or more image acquisition devices selected from the plurality of image acquisition devices based on the interfering modalities.

20. A non-transitory computer-readable medium comprising instructions that, when executed by at least one processor, cause the at least one processor to perform one or more operations comprising:

obtaining acquisition data;

prioritizing selection, based on the acquisition data, of one or more image acquisition devices from a plurality of image acquisition devices in accordance with predetermined criteria, the predetermined criteria including a computational load, image acquisition device availability, image acquisition device cost, one or more use cases, or any combination thereof, the plurality of image acquisition devices configured to be received in any one of a plurality of slots that each comprise a predetermined shape, the respective ones of the one or more image acquisition devices including a different modality; and controlling, based on the prioritized selection, operation of the one or more image acquisition devices selected from the plurality of image acquisition devices.

* * * * *